US00PP08229P

United States Patent [19]

Christensen

[11] Patent Number: Plant 8,229

[45] Date of Patent: May 18, 1993

[54] ROSE PLANT JACTUTTI

[75] Inventor: Jack E. Christensen, Ontario, Calif.

[73] Assignee: Bear Creek Gardens, Inc., Medford, Oreg.

[21] Appl. No.: 775,245

[22] Filed: Oct. 10, 1991

[51] Int. Cl.[5] ..... A01H 5/00
[52] U.S. Cl. ..... Plt./7.1
[58] Field of Search ..... Plt. 7.1, 8.2

*Primary Examiner*—James R. Feyrer
*Assistant Examiner*—E. F. McElwain
*Attorney, Agent, or Firm*—Klarquist, Sparkman, Campbell, Leigh & Whinston

[57] ABSTRACT

Minature rose with yellow-orange blossom petals having red stripes which spread as blossom ages. Plant is resistant to rust and powdery mildew. Rose is cross of variety AROgobi with the variety MORprints.

1 Drawing Sheet

The present invention relates to a new and distinct variety of rose plant of the miniature class which was originated by me by crossing the variety AROgobi, U.S. Plant Pat. No. 5,702, with the variety MORprints.

The primary objective of this breeding was to produce a new rose variety having the gold yellow colour and dark green foliage of the variety AROgobi combined with the compact habit and flower striping of the variety MORpints. The objective was substantially achieved along with other desirable improvements as evidenced by the following unique combination of characteristics which are outstanding in the new variety and which distinguish it from its parents, as well as from all other varieties of which I am aware:

1. Unusual striping in the flower and a gradual spread of the red color in the flower as it ages.
2. Resistance to powdery mildew and rust
3. Dark green glossy foliage
4. Upright but dwarf habit of growth
5. Abundance of glands on stipules, sepals, peduncle and petiole.

Asexual reproduction of this new variety by budding and by softwood cuttings, as performed at Wasco and Somis, Calif., shows that the foregoing characteristics and distinctions come true to form and are established and transmitted through succeeding propagations.

The accompanying photograph shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:
*Seed parent.*—AROgobi.
*Pollen parent.*—MORpints.
Classification:
*Botanical.*—*Rosa hybrida.*
*Commercial.*—Miniature.

FLOWER

Observations made from specimens grown in a garden in Somis, Calif., Apr.-Jun. of 1991.

Blooming habit: Continuous.
Bud:
*Size.*—¾ inch when the petals start to unfurl.
*Form.*—Short, pointed ovoid to globular.
*Color.*—When sepals first divide, bud color is Yellow-Orange Group 15B with the petals tipped in Red Group 46B. When half blown, the upper sides of the petals are Yellow-Orange Group 15B with petal edges and stripes in Red Group 40D; and the lower sides of the petals are Yellow-Orange Group 15B with the outside petals tipped in Red Group 46B.
*Sepals.*—Color: Green Group 137D. Surface texture: Covered in fine hairs. There are three lightly appendaged sepals that are edged with glands. There are two unappendaged sepals with hairy edges.
*Receptacle.*—Color: Green Group 137D. Shape: Funnel. Size: ¼"×¼". Surface: Hairy.
*Peduncle.*—Length: Short, one inch. Surface: Glandular. Color: Medium green. Strength: Stiff, erect, slender.
Bloom:
*Size.*—Small. Average open size is 1½ inches.
*Borne.*—Several together, in flat clusters.
*Stems.*—Short, strong, 6".
*Form.*—When first open: High centered. Permanence: Flattens.
*Petalage.*—Number of petals under normal conditions: 25-30.
*Color.*—The upper side of the petals is Yellor-Orange Group 15B with petal edges and stripes in Red Group 40D. The reverse side of the petals is Yellow-Orange Group 15B with the outside row of petals tipped in Red Group 46B. The color of the base of petals is Yellow-Orange Group 15B. The major color on the upper side is Yellow-Orange Group 15B.
*Variegations.*—No variegations except the striping.
*Discoloration.*—The general tonality at the end of the first day: No change. At the end of the third day, a gradual intensification and spread of the red coloration as the flower ages. The striping is most evident in cool sunny weather. In hot weather, the striping can be masked by the rapid change in color from bright yellow to red.
*Fragrance.*—Slight.
Petals:

*Texture.*—Medium.
*Shape.*—Deltoid.
*Form.*—Tips slightly recurved, edges slightly quilled.
*Arrangements.*—Imbricated, with no petaloids in the center.
*Persistence.*—Drop off cleanly.
*Lastingness.*—On the plant: short, 3–4 days. As a cut flower: short, 4 days.

Reproductive parts:
*Anthers.*—Size: Medium. Quantity: Many. Color: Yellow. Arrangement: Regular around styles.
*Filaments.*—Color: Yellow.
*Pollen.*—Color: Gold-yellow.
*Styles.*—Color: White.
*Stigmas.*—Color: Greenish-white.

Form: Bush.

Growth: Vigorous; dwarf; upright; branching.

Foliage:
*Number of leaflets on normal mid-stem leaves.*—or 7.
*Size.*—Small, 3½" long×2" wide.
*Quantity.*—Abundant.
*Color.*—New foliage: dark green with a reddish cast. Old foliage: dark green and glossy.

Leaflets:
*Shape.*—Pointed oval.
*Texture.*—Upper side: Leathery, glossy.
*Edge.*—Serrated.
*Serration.*—Single.

*Petiole rachis.*—Color: Reddish, becoming green as the leaf ages.
*Petiole underside.*—Rough with prickles and glands.
*Stipules.*—Medium, ½"; bearded and lower surface covered in glands.
*Disease resistance.*—Resistant to rust and mildew under normal growing conditions at Somis, Calif.

Wood:
*New wood.*—Color: Reddish. Bark: Smooth.
*Old wood.*—Color: Green. Bark: Smooth.

Prickles:
*Quantity.*—On main canes from base: ordinary. On laterals from main canes: ordinary.
Form.—Short, hooked downward.
*Color when young.*—Green.

Small prickles:
*Quantity.*—On main stalks: Few. On laterals: Few.

I claim:

1. A new and distinct variety of rose plant of the miniature class, substantially as herein shown and described, characterized particularly as to novelty by the unique combination of its novel striping and color change in the flower, the presence of glands on the stipules, peduncle, petiole and rachis, its resistance to powdery mildew and rust, its upright but dwarf growth habit and its dark green glossy foliage.

* * * * *

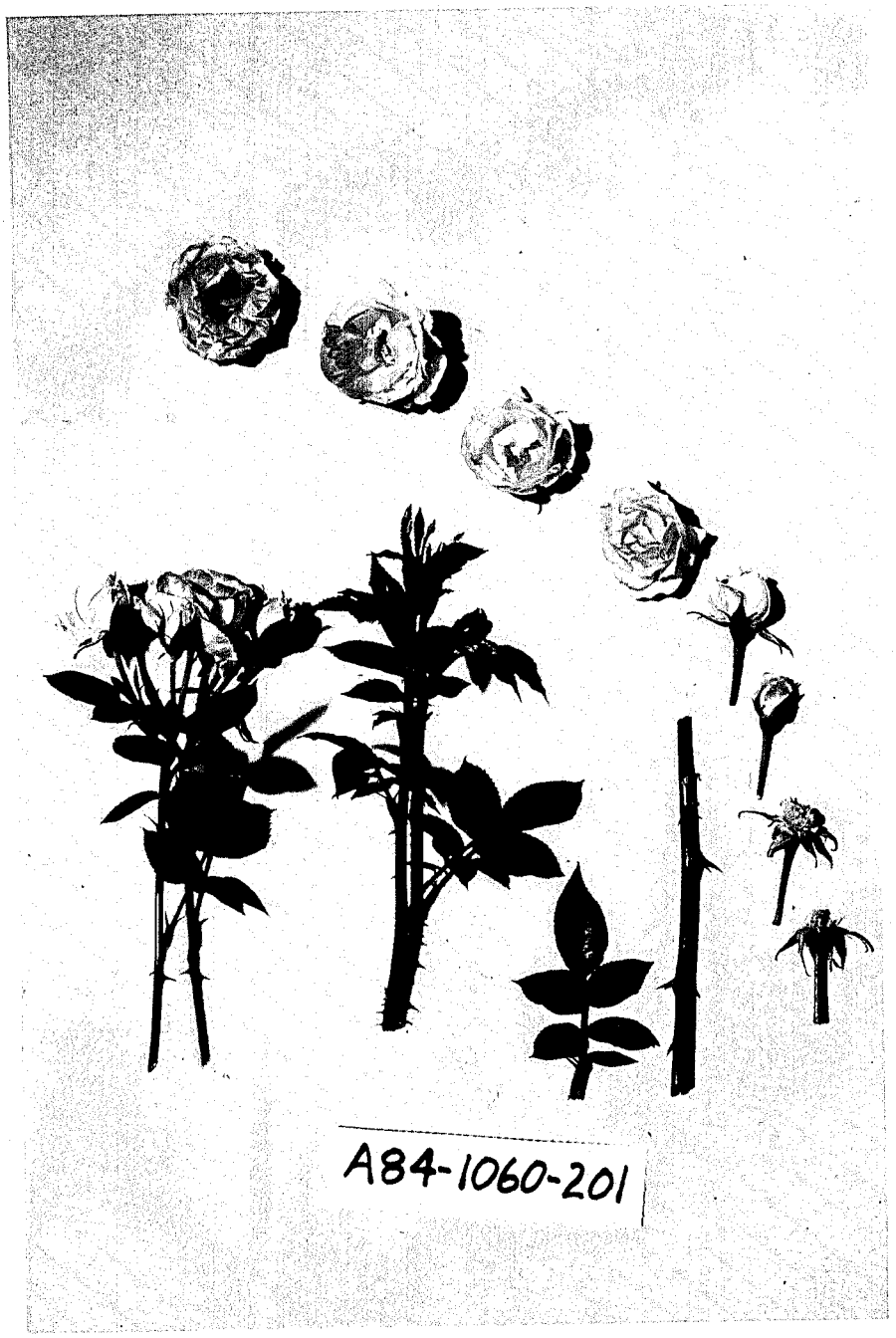
A84-1060-201